(12) United States Patent
Highsmith et al.

(10) Patent No.: US 6,603,018 B2
(45) Date of Patent: Aug. 5, 2003

(54) PROCESS FOR THE SYNTHESIS AND RECOVERY OF NITRAMINES

(75) Inventors: Thomas K. Highsmith, North Ogden, UT (US); Jami M. Hanks, Logan, UT (US); Stephen P. Velarde, Ogden, UT (US); Jeffrey Bottaro, Mountain View, CA (US)

(73) Assignee: Alliant Techsystems Inc., Edina, MN (US)

( * ) Notice: Subject to any disclaimer, the term of this patent is extended or adjusted under 35 U.S.C. 154(b) by 0 days.

(21) Appl. No.: 10/060,051

(22) Filed: Jan. 29, 2002

(65) Prior Publication Data

US 2002/0156291 A1 Oct. 24, 2002

Related U.S. Application Data

(60) Provisional application No. 60/266,030, filed on Feb. 1, 2001.

(51) Int. Cl.$^7$ .............................................. C07D 249/08
(52) U.S. Cl. ................. 548/267.2; 548/327.1; 548/265.2; 548/316.4; 564/109; 564/107
(58) Field of Search ........................... 548/265.2, 316.4, 548/267.2, 327.1; 564/109, 107

(56) References Cited

U.S. PATENT DOCUMENTS

| | | |
|---|---|---|
| 4,085,123 A | 4/1978 | Flanagan et al. |
| 5,243,075 A | 9/1993 | Cason-Smith |
| 6,255,512 B1 | 7/2001 | Bottaro et al. |

OTHER PUBLICATIONS

George F. Wright, Methods of formation of the nitramino group, its properties and reactions, The Chemistry of the nitro and nitroso groups, 1969, 613–637, Interscience Publishers.

F. Albert Cotton, et al., Advanced Inorganic Chemistry, 1980, 226–228, 4$^{th}$ Edition, John Wiley & Sons, Canada.

J. Majer, et al., Synthesen Auf Dem Gebiet Der Nitramine, Collection Czechoslov, Chem. Commum., vol. 31, 1966, 2547–2557, XP002199283, Prague CS.

H. Yan, Synthesis of High Density Azidonitramines, Department of Chemistry and Environmental Engineering, Beijing Polytechnic University, 135–1 to 135–5.

51 Propellants and Explosives, Chemical Abstracts, 1962, 3685–86.

10B–Aliphatic Compounds, Chemical Abstracts, 5129–5132.

Chemical Abstracts, vol. 52, 14275–14276.

Chemical Abstracts, vol. 51, 9163–9164.

Charles W. Sauer, et al., Nitramines. I. Methylenedinitramine, vol. 77, 1954, 2560–2561.

Charles W. Sauer, et al., Preparation of Methylenedinitramine, vol. 77, 1954, 2559–2560.

Database Crossfire Beilstein Online! Beilstein Institut zur Forderung der Chemischen Wissenschaften, Frankfurt am Main, DE; BRN=7304868, XP002199284, abstract & Russ. J. Org. Chem., vol. 30, No. 5.2, 1994, 813–817.

*Primary Examiner*—Ceila Chang
*Assistant Examiner*—Rei-Tsang Shiao
(74) *Attorney, Agent, or Firm*—TraskBritt

(57) ABSTRACT

A method is provided for the synthesis of nitramines and the recovery of the nitramines from a clathrate.

12 Claims, 12 Drawing Sheets

PROCESS FOR THE SYNTHESIS AND RECOVERY OF NITRAMINES

RELATED APPLICATION

This application claims the benefit of priority of U.S. provisional application 60/266,030 filed in the U.S. Patent & Trademark Office on Feb. 1, 2001, the complete disclosure of which is incorporated herein by reference.

GOVERNMENT LICENSING RIGHTS

The U.S. Government has a paid-up license in this invention and the right in limited circumstances to require the patent owner to license others on reasonable terms as provided for by the terms of contract F04611-99-C-0010 awarded by the Air Force Research Lab.

BACKGROUND OF THE INVENTION

1. Field of the Invention

This invention generally relates to the synthesis and recovery of energetic materials, especially for use in gun and rocket propellants and explosives. More specifically, the invention relates to the synthesis and recovery of nitramines.

2. Description of the Related Art

Nitramines are highly energetic compounds having found wide acceptance in the art of explosives and rocket propellant. The most common nitramines in use in the explosives and propellant arts today are 1,3,5-trinitro-1,3,5-triazacyclohexane (RDX) and 1,3,5,7-tetranitro-1,3,5,7-tetraazacyclooctane (HMX). The acceptance of RDX and HMX in the art is generally attributed to the high energetic performance and the high energy density possessed by these compounds. In essence, RDX and HMX are the standards of energetic performance and energy density by which other energetic compounds are measured.

A drawback to RDX and HMX is that these nitramine compounds are relatively sensitive to shock, friction, and impact. The high sensitivities associated with RDX and HMX make these nitramine compounds less desirable for some applications, especially where the compounds are used or stored in an environment in which traumatic stresses may be encountered. By way of example, in a military conflict, the traumatic impact of hostile ammunition into a rocket motor or weaponry carrying RDX or HMX can lead to destruction of surrounding objects and loss of human life. In the event that the impacted rocket motor or weaponry is in proximity to arsenal or other explosive or combustible materials, catastrophic damage may result.

There is thus a need in the art to provide a highly energetic and high energy density compound that is relatively insensitive to physical stimuli, such as shock, impact, and friction. Various other nitramine compounds have been synthesized towards this end. For example, U.S. Pat. No. 4,085,123 to Flanagan et al. describes the synthesis of the nitramine compound 1,3-diazido-2-nitrazapropane (DANP) as an energetic liquid plasticizer for solid propellants. According to Flanagan et al., the DANP azide plasticizer is synthesized by generating a solution of 1,3-diacetoxy-2-nitrazapropane and dioxane and saturating the solution with anhydrous chloride gas. The use of anhydrous chloride gas makes this process extremely hazardous. In this regard, the Flanagan et al. patent states that the resulting DANP plasticizer is sensitive and must be handled with caution. Moreover, the acetate and chloride precursors are inherently impure, since their reactions reach and remain at equilibrium. In order to minimize the impurities, Flanagan et al. teach distilling both the 1,3-diacetoxy-2-nitrazapropane precursor and its chlorine analogue prior performing the reactions. On an industrial scale, these distillation techniques are impractical and highly hazardous.

Another nitramine synthesis route is disclosed in U.S. Pat. No. 5,243,075 to Cason-Smith, which describes contacting an N-acetoxymethyl nitramine with a mixture of concentrated hydrochloric acid and trifluoroacetic acid to produce the corresponding N-chloromethyl nitramine analogue. The chlorinated nitramines produced by this process are not sufficiently robust or chemically stable for effective use as an energetic material. The chlorine atoms of the N-chloromethyl nitramines are inherently unstable. When heated, hydrogen chloride gas is released. The presence of the HCl acid can lead to degradation of the material via autocatalysis.

The synthesis of 1,3-bis-(3'5'-dinitro-1',2',4'-triazolo)-2-nitrazapentane (BNTN) is also known. BNTN has the following structure:

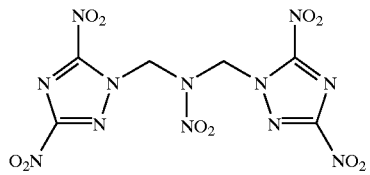

Specifically, it is known to produce BNTN by suspending sodium dinitro-1,2,4-triazole in dry acetonitrile, and adding 2-nitraza-1,3-dichloropropane. It is believed by the inventors that the 2-nitraza-1,3-dichloropropane is prepared by reacting 2-nitraza-1,3-diacetoxypropane with an inorganic chlorinating agent, such as phosphorus pentachloride ($PCl_5$). According to this method, however, the 2-nitraza-1,3-diacetoxypropane must be purified by distillation prior to chlorination to avoid the formation of chlorine by-products. Another distillation step is needed prior to the reaction of the 2-nitraza-1,3-dichloropropane with the sodium salt of dinitro-1,2,4-triazole. The hazardous nature and toxicity of 2-nitrazapropane and its by-products make distillation highly undesirable and impractical to produce on an industrial scale. Further, the 2-nitraza-1,3,-dichloropropane is very electrophilic and may react with incidental moisture to replace the chlorine atoms and form hydroxymethyl nitramines, thus complicating the nucleophilic addition of the triazole.

The inventors have found that the technique disclosed in the Cason-Smith patent is not suitable for making BNTN. The conditions set forth in the Cason-Smith patent—e.g., treating with HCl and trifluoroacetic acid—were insufficient to drive the reaction of 2-nitraza-1,3-diacetoxypropane and, as a consequence, a largely impure product was obtained.

SUMMARY OF THE INVENTION

This invention provides a synthesis route for preparing and recovering nitramine compounds having one or more N-heterocyclomethyl groups. The nitramine compounds preferably possess relatively high energetic performance, comparable or superior energy density, and relatively low sensitivity to physical stimuli (e.g., shock, friction, and impact) in relation to the current standards of RDX and HMX.

This invention also provides a method by which an N-heterocyclomethyl polynitrazaalkane can be precipitated at high yields from a solvent that forms a clathrate with the N-heterocyclomethyl polynitrazaalkane.

This invention further provides a method for synthesizing a triazole, such as 3,5-dinitro-1,2,4-triazole.

This invention still further provides a method for synthesizing a salt of a triazole, especially dinitrotriazole.

It is to be noted that, as used in the specification and the appended claims, the singular forms "a," "an," and "the" include plural referents unless the context clearly dictates otherwise. Thus, by way of example, the term "polynitrazaalkane" includes in its definition not only a single polynitrazaalkane, but also a combination of two or more polynitrazaalkanes.

The term "polynitrazaalkane" means a nitrazaalkane having two or more nitraza (nitramine) groups. A nitraza group may be internally positioned along the azaalkane chain, or can be at a terminal position.

In accordance with an aspect of this invention, N-acetoxymethyl nitrazaalkane having an azaalkane chain (or backbone) of at least five atoms is halogenated to form an N-halomethyl nitrazaalkane. The N-halomethyl nitrazaalkane comprises at least one halomethyl moiety having a halogen atom, with the halogen atom comprising chlorine, bromine, or iodine. A salt of a heterocyclic nucleophile is reacted with the N-halomethyl nitrazaalkane to form an N-heterocyclomethyl nitrazaalkane. The solvent in which the nucleophilic substitution takes place forms a clathrate with the N-heterocyclomethyl nitrazaalkane. In accordance with the teachings of this invention, the N-heterocyclomethyl nitrazaalkane may be precipitated in a nonsolvent and recovered from the nonsolvent.

In accordance with another aspect of this invention, a method is provided for N-heterocyclomethylating a terminal nitraza moiety or terminal nitraza moieties of a polynitrazaalkane. In accordance with the teachings of this invention, the N-heterocyclomethyl polynitrazaalkane may be precipitated in a nonsolvent and recovered.

In accordance with still another aspect of this invention, a method is provided for preparing 3,5-dinitro-1,2,4-triazole or a salt thereof. The method comprises nitrating 3,5-diamino-1,2,4-triazole in an acidic solution having a pH not greater than about 3 to form 3,5-dinitro-1,2,4-triazole. The 3,5-dinitro-1,2,4-triazole is extracted from the acidic solution with little or no neutralization, so that the pH of the acidic solution during extraction is no greater than about 3. Optionally, the 3,5-dinitro-1,2,4-triazole may then be treated with a base to form a 3,5-dinitro-1,2,4-triazole salt.

BRIEF DESCRIPTION OF THE DRAWINGS

The accompanying drawings are incorporated in and constitute a part of the specification. The drawings, together with the general description given above and the detailed description of the preferred embodiments and methods given below, serve to explain the principles of the invention. In such drawings.

DETAILED DESCRIPTION OF PREFERRED EMBODIMENTS AND METHODS OF THE INVENTION

Reference will now be made in detail to the presently preferred embodiments and methods of the invention as described below. It should be noted, however, that the invention in its broader aspects is not limited to the specific details, representative devices and methods, and examples described in this section in connection with the preferred embodiments and methods. The invention according to its various aspects is particularly pointed out and distinctly claimed in the attached claims read in view of this specification, and appropriate equivalents.

Figure 1:
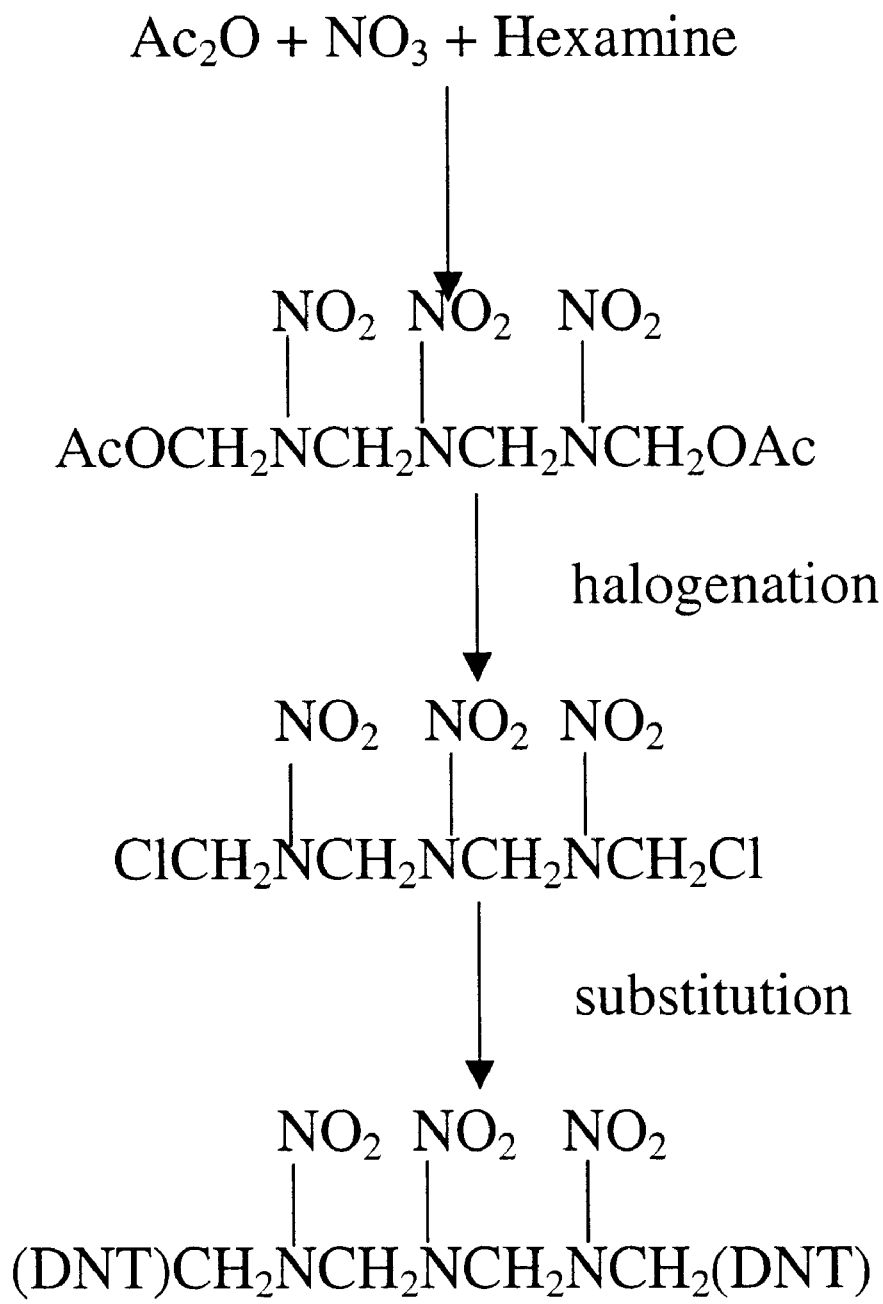
FIG. 1 is a flow chart setting forth a procedure for preparing 1,7-bis-(3',5'-dinitro-1',2',4'-triazolo)-2,4,6-trinitrazaheptane in accordance with an embodiment of this invention.
Figure 2:
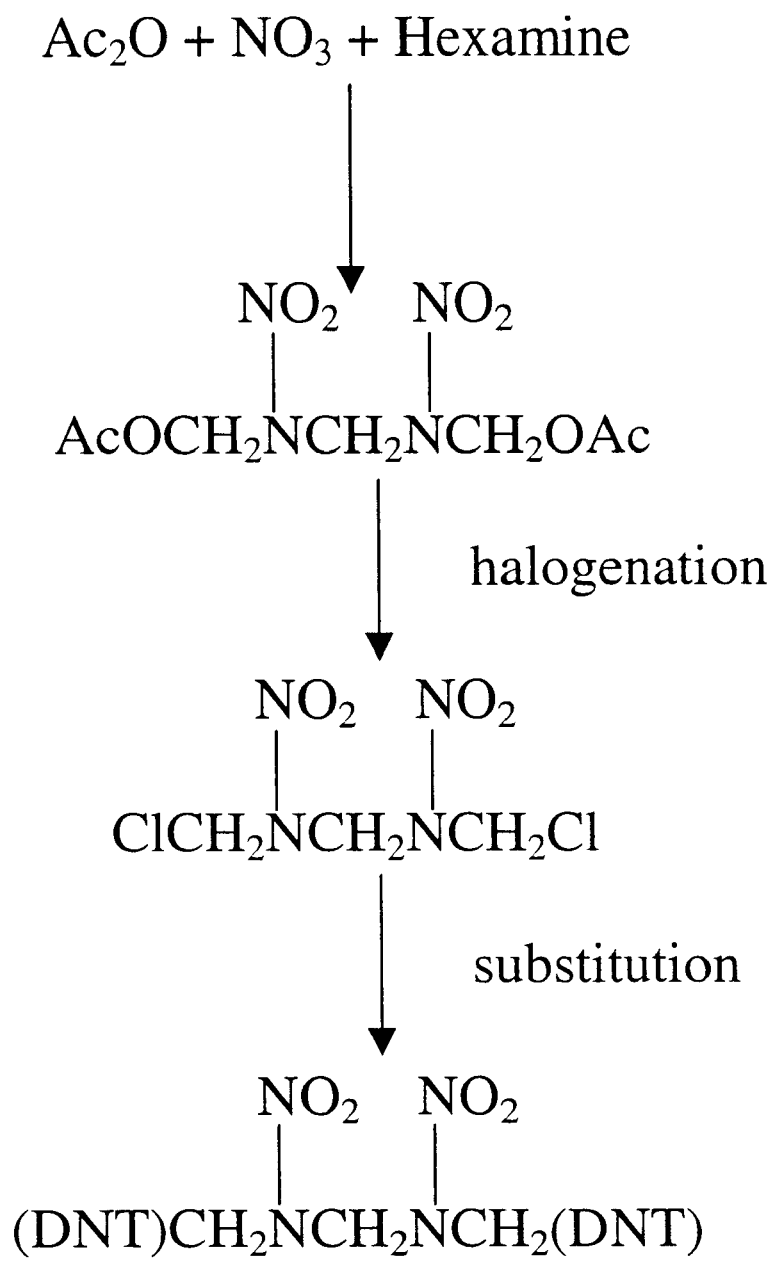
FIG. 2 is a flow chart setting forth a procedure similar to that of FIG. 1, but used to prepare 1,5-bis-(3',5'-dinitro-1',2',4'-triazolo)-2,4-dinitrazapentane.
Figure 3:
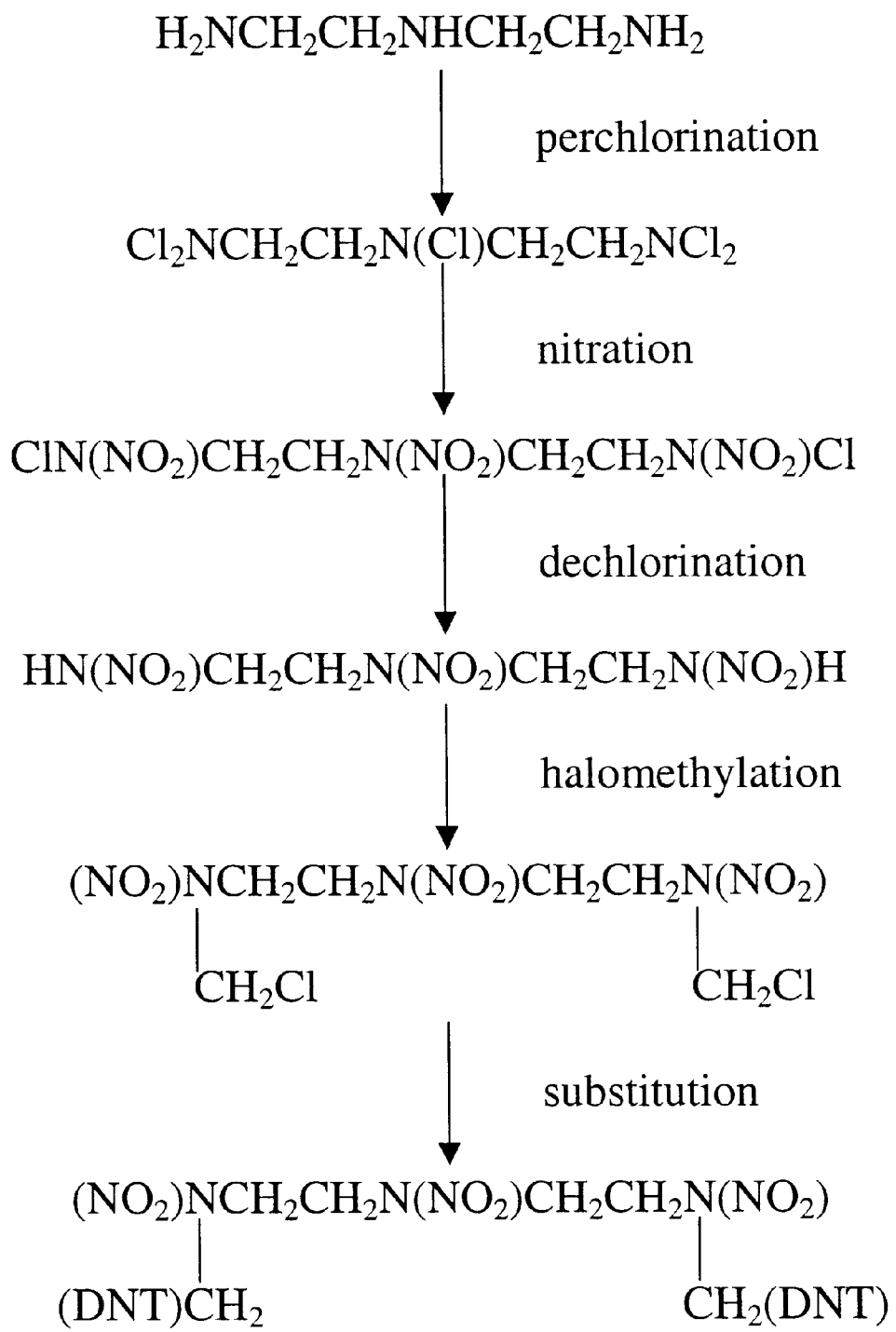
FIG. 3 is a flow chart setting forth a procedure for preparing 1,9-bis-(3',5'-dinitro-1',2',4'-triazolo)-2,5,8-trinitrazanonane in accordance with another embodiment of this invention.
Figure 4:
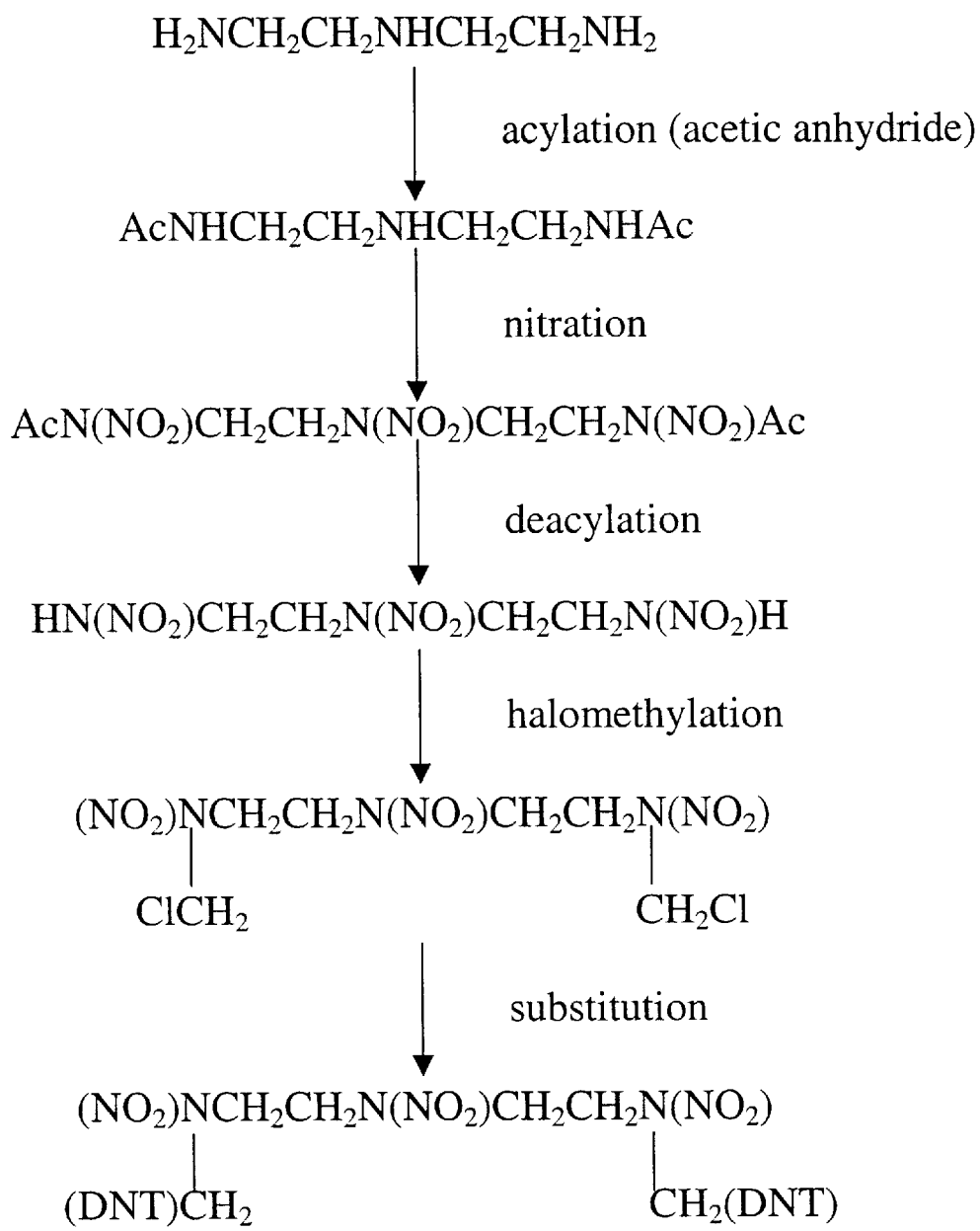
FIG. 4 is a flow chart setting forth a procedure for preparing 1,9-bis-(3',5'-dinitro-1',2',4'-triazolo)-2,5,8-trinitrazanonane in accordance with still another embodiment of this invention.
Figure 5:
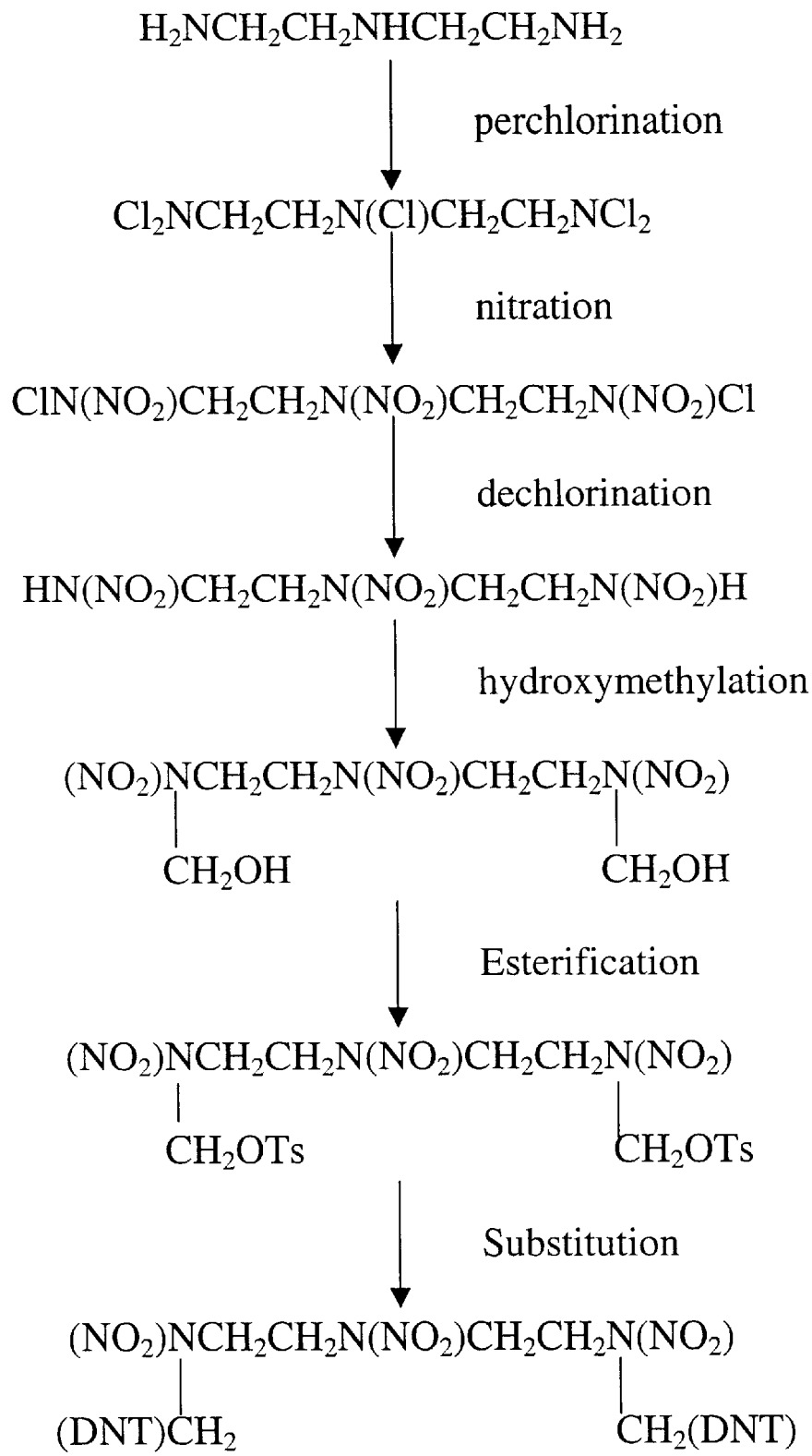
FIG. 5 is a flow chart setting forth a procedure for preparing 1,9-bis-(3',5'-dinitro-1',2',4'-triazolo)-2,5,8-trinitrazanonane in accordance with a further embodiment of this invention.
Figure 6:
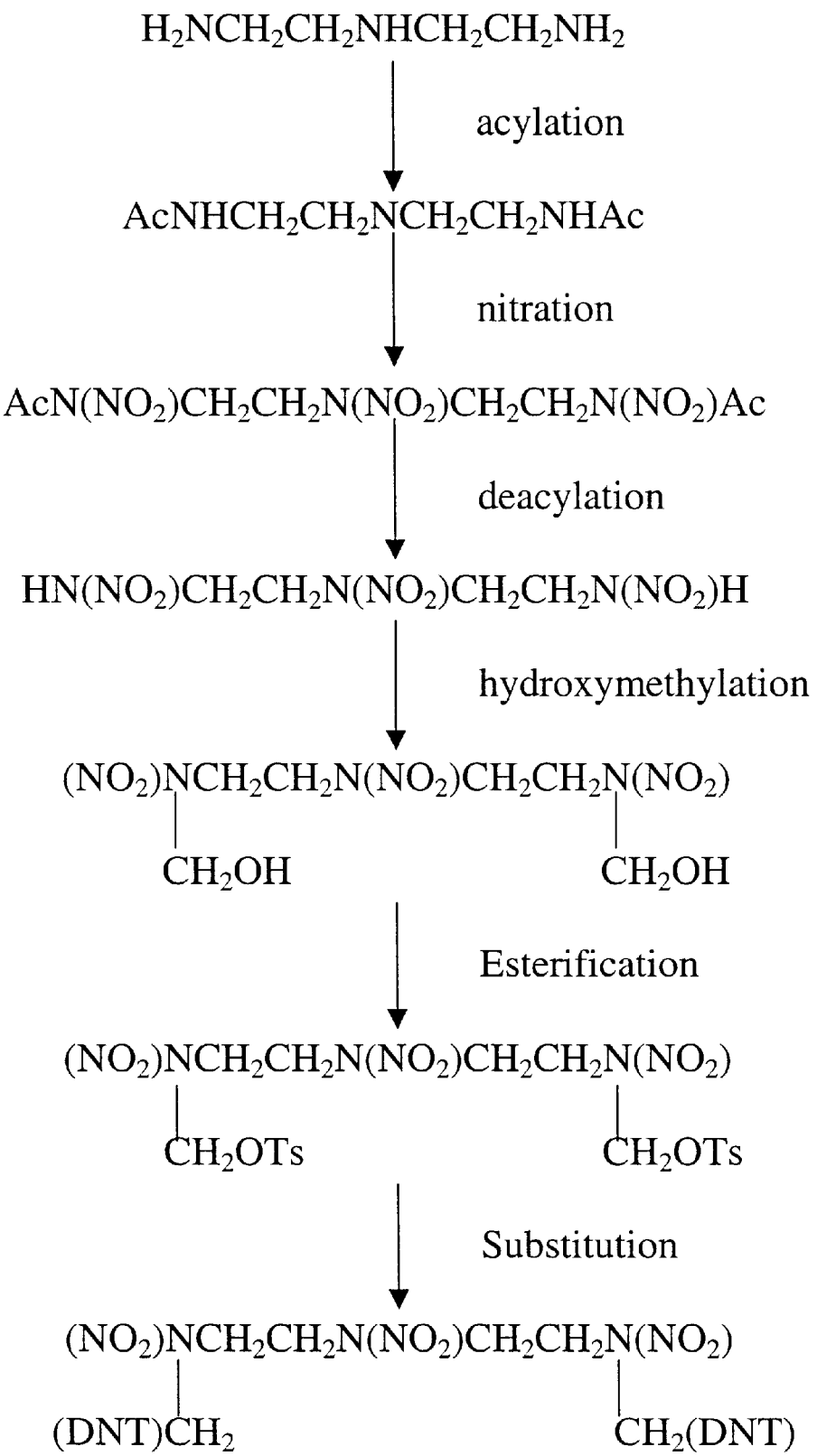
FIG. 6 is a flow chart setting forth a procedure for preparing 1,9-bis-(3',5'-dinitro-1',2',4'-triazolo)-2,5,8-trinitrazanonane in accordance with still a further embodiment of this invention.
Figure 7:
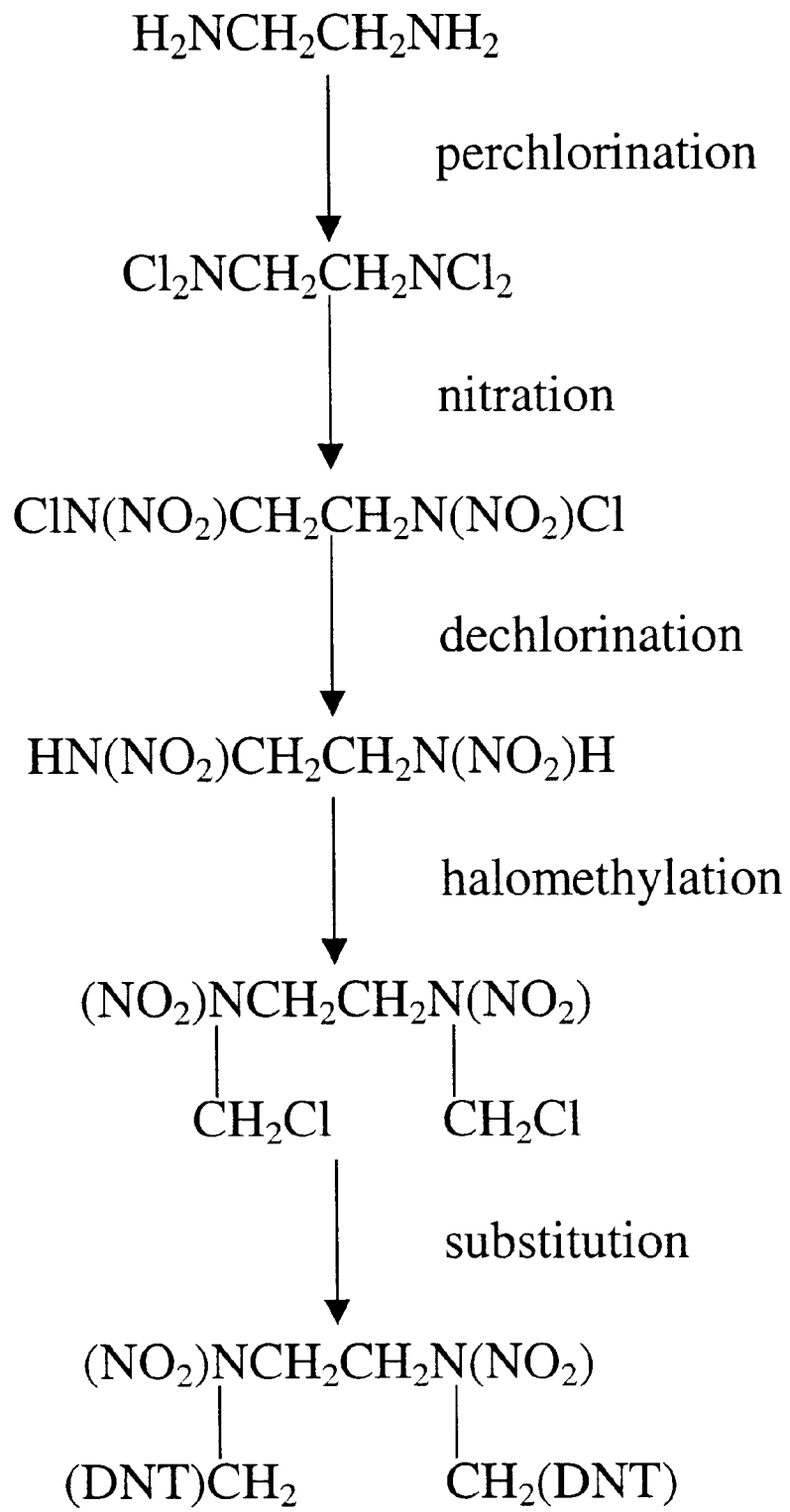
FIG. 7 is a flow chart similar to FIG. 3, setting forth a procedure for preparing 1,6-bis-(3',5'-dinitro-1',2',4'-triazolo)-2,5-dinitrahexane.
Figure 8:
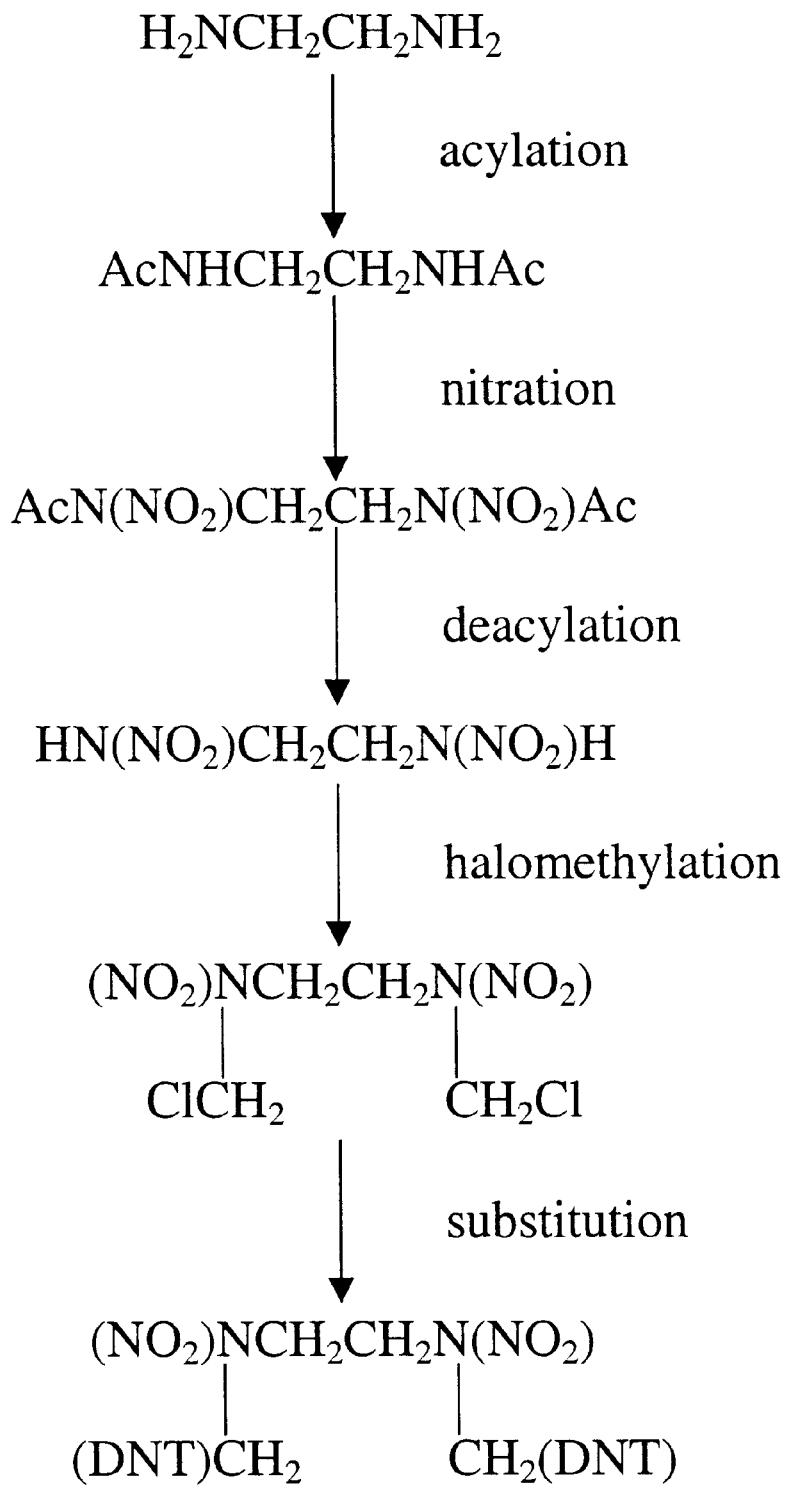
FIG. 8 is a flow chart similar to FIG. 4, setting forth a procedure for preparing 1,6-bis-(3',5'-dinitro-1',2',4'-triazolo)-2,5-dinitrahexane.

A method of preparing an N-heterocyclomethyl nitrazaalkane in accordance with one preferred embodiment of the invention is generally shown in FIGS. 1 and 2. Referring more particularly to FIG. 1, there is shown a method of making 1,7-bis-(3',5'-dinitro-1',2',4'-triazolo)-2,4,6-trinitrazaheptane (BNTH). An N-diacetoxymethyl nitrazaalkane precursor is first prepared in any manner known in the art. The synthesis of this precursor—1,7-diacetoxy-2,4,6-trinitrazaheptane—may be performed by reacting diacetate, hexamine, and nitric acid. The synthesis of 1,7-diacetoxy-2,4,6-trinitrazaheptane is described in U.S. Pat. No. 5,243,075, the disclosure of which is incorporated herein by reference. The N-diacetoxymethyl nitrazaalkane is halogenated to replace the acetoxy moieties with a halogen atom, such as chlorine, bromine, or iodine. The halogenation may comprise chlorinating with, for example, a mixture comprising concentrated hydrochloric acid and trifluoroacetic acid, or a combination of phosphorus pentachloride in a solvent. The halogenation is preferably conducted in a solvent comprising at least one member selected from the group consisting of methylene chloride, chloroform, and dioxane. The resulting dichloride nitramine may optionally be recrystallized prior to further processing.

Next, the 1,7-dichloro-2,4,6-trinitrazaheptane is subject to a nucleophilic replacement with a salt of a substituted heterocycle group. The heterocyclic ring may be aromatic or nonaromatic, although aromatic rings are currently preferred. Examples of heterocycles that may be used in this embodiment and the other embodiments described in the summary above and this detailed description include five and six member rings containing at least one endocyclic heteroatom. Representative 5-membered and 6-membered heterocyclic rings include triazoles, imidazoles, pyrazoles, oxazoles, isoxazoles, and tetrazoles. This list is not intended to be exhaustive. Additionally, three and four member heterocycle rings that may be used include, for example, aziridines and azetidines. The heterocylic groups may be substituted with one or more exocyclic ring substituents, such as, by way of example, nitro groups, azido groups, and amino groups. Nitro substituents are preferred. Preferred nucleophiles include mononitrotriazole, dinitrotriazole, mononitroimidazole, dinitroimidazole, and trinitroimidazole.

The nucleophile is typically introduced into the reaction as a salt. Suitable cations for the nucleophile include potassium, sodium, lithium, and tetraalkyl ammonium (alkyls are the same or different and are each preferably 1 to 4 carbon atoms).

The reaction of potassium 3,5-dinitrotriazolate with the chloromethyl-nitramine electrophiles is greatly facilitated by the inclusion of two equivalents of sodium bromide in the reaction. In effect, this salt mediates an in-situ transhalogenation. The reaction is much cleaner, because the reaction proceeds more quickly. When the reaction is complete, the sodium chloride and potassium bromide are removed by filtration. The organic solvent, THF, is then removed in vacuum and the residue partitioned between water and ethyl acetate. Two or three water washes serve to remove all of the starting materials and byproducts. After drying and removal of the ethyl acetate, the residue is recrystallized from THF/MTBE.

The nucleophilic replacement takes place in one or more solvents. Representative solvents for this reaction include one or more members selected from the group consisting of acetonitrile, dioxane, low molecular weight alcohols (e.g., methanol, ethanol, and propanol), and tetrahydrofuran.

The inventors have found that the heterocyclonitramines produced by this and other processes described in this detailed description are extremely difficult to isolate as pure solids from the solvents. One partially successful approach was to precipitate the entire reaction mixture, including THF, unreacted KDNT, KBr, NaCl, and byproducts, directly into water. Although the THF remained occluded, the other materials were successfully removed.

While not wishing to be bound by any theory, it is believed that the reason for this difficulty is solvent occlusion, generally thought to be in the form of a clathrate. A clathrate is generally understood in the art to mean an inclusion complex, such as in the case wherein molecules of one substance contain an open structure, such as cavities, holes, or channels, typically in a crystalline structure, in which atoms or molecules of another substance are trapped or held.

The inventors have found that the N-heterocyclomethyl nitrazaalkanes produced by this and other embodiments of the invention can be recovered from the clathrates by precipitation. Generally, the solvent-occluded heterocyclomethyl nitramine is fully dissolved in its solvent so that no (or substantially no) solid nitramine remains. The solution is then precipitated into a nonsolvent at such a rate that crystals form rapidly, permitting only incidental amounts of solvent to be included in the crystal structure. Preferably, precipitation is performed by adding the nitramine-containing solution to the nonsolvent slowly, more preferably dropwise. The volumetric ratio of nonsolvent to nitramine-containing solution is preferably at least 2:1, preferably at least 3:1. Surprisingly, methanol has been found to be a particularly favorable nonsolvent for the precipitation of BNTH and other nitramines produced within the scope of this invention. Methylene chloride is also a suitable nonsolvent for the precipitation.

FIG. 2 illustrates a method of making 1,5-bis-(3',5'-dinitro-1',2',4'-triazolo)-2,4-dinitrazapentane (BNDP) in a manner similar to that of FIG. 1. Synthesis of the 1,5-diacetoxy-2,4-dinitrazapentane is also known in the art and can be performed without undue experimentation, especially in view of U.S. Pat. No. 5,243,075 to Cason-Smith.

The nitramines illustrated in FIGS. 1 and 2 contain methylene spacers between the nitraza (nitramine) moieties of the azaalkane. Another representative higher homologue having three methylene spacers is 1,9-bis-(3',5'-dinitro-1',2',4'-triazolo)-2,4,6,8-tetranitrazapentane. It is to be understood that dimethylene (i.e., ethylene) or other multimethylene spacers may be present in the azaalkane chain (in addition to or as an alternative for the methylene spacers). The azaalkane chain may also be branched, with the branches optionally containing nitraza moieties and/or a terminal cite for nucleophilic substitution of a heterocyclic moiety. It is also possible to make a heterocyclomethyl nitrazaalkane having only a single heterocyclic moiety, such as by starting with a mono-acetoxy-nitrazaalkane, such as one selected from the group consisting of 1-acetoxy-2,4,6-trinitrazaheptane, 1-acetoxy-2,4-dinitrazapentane, and 1-acetoxy-2,4,6,8-tetranitrazanonane. Another possibility is for one or more of the terminal moieties to be substituted with an energetic functionality other than a heterocylomethyl group, for example, an azido group, so long as at least one heterocyclomethyl group is present in the molecule.

FIGS. 3–12 illustrate a representative, but not exhaustive, set of exemplary synthesis routes for preparing heterocyclomethyl polynitramines. Each of these synthesis routes comprises the recovery of the N-heterocyclomethyl polynitrazaalkane from a clathrate by precipitation in a nonsolvent.

As illustrated in FIGS. 3, 4, and 7–9, the polynitrazaalkanes may be heterocyclomethylated by halomethylating the polynitrazaalkane with, for example, paraformaldehyde and a halogenating agent to form an N-halomethyl polynitrazaalkane. In the illustrated examples, the halogenating agent may be selected from the group of hydrogen chloride, phosphorus pentachloride, sulfurial chloride, and thionyl chloride, with hydrogen chloride being preferred. The halomethylating may be performed at room temperature or lower. Depending upon the selected halogenating agent, volatiles may be evaporated, and the product recrystallized from a suitable solvent. The heterocyclic nucleophile replaces the halogen atom of the N-halomethyl polynitrazaalkane to form the N-heterocyclomethyl polynitrazaalkane. Suitable solvents include acetonitrile, tetrahydrofuran, dimethylformamide, dimethyl sulfoxide, N-methylpyrrolidone, diethyl ether, or mixtures thereof.

Another embodiment for heterocyclomethylating the polynitrazaalkane is illustrated in FIGS. 5, 6, and 10–12. According to this embodiment, the terminal nitraza moiety of the polynitrazaalkane is hydroxymethylated to form at least one N-hydroxymethyl nitraza moiety. This reaction may occur in water, optionally with a cosolvent such as acetonitrile, tetrahydrofuran, dimethylformamide, dimethyl sulfoxide, N-methylpyrrolidone, or mixtures thereof. The next step involves esterifying the N-hydroxymethyl nitraza moiety of the polynitrazaalkane with a leaving group. Suitable leaving groups include: benzene sulfonates and benzene sulfonates substituted with alkyl(s) and/or halogen atom(s), such as tosylate and brosylate; alkane sulfonates, such as methane sulfonate; and halogen-substituted alkane sulfonates, such as trifluoromethane sulfonate. The heterocyclic nucleophile is then substituted for the leaving group of the polynitrazaalkane to form an N-heterocyclomethyl polynitrazaalkane. Generally, chlorinated hydrocarbon solvents such as, for example: chloroform, methylene chloride, 1,2-dichloroethane; and polar organic solvents including tetrahydrofuran and dioxane and the like may be used. Pyridine and substituted pyridines may be used as a proton scavenger in this reaction.

Representative heterocycles that may be used in the embodiments illustrated in FIGS. 3–12 include five and six member rings containing at least one endocyclic heteroatom, especially triazoles, imidazoles, pyrazoles, oxazoles, isoxazoles, and tetrazoles. Additionally, three and four member heterocycle rings that may be used include aziridines and azetidines. The heterocyclic groups may be substituted with one or more exocyclic ring substituents, such as nitro groups, azido groups, and amino groups. Preferred nucleophiles include mononitrotriazole, dinitrotriazole, mononitroimidazole, dinitroimidazole, and trinitroimidazole. The heterocylic nucleophile is reacted in a suitable solvent, such as, for example, acetonitrile, dioxane, low molecular weight alcohols (e.g., methanol, ethanol, and propanol), and tetrahydrofuran, dimethylformamide, dimethyl sulfoxide, N-methylpyrrolidone, diethyl ether, or mixtures thereof.

FIGS. 3–6 illustrate the synthesis of 1,9-bis-(3',5'-dinitro-1',2',4'-triazolo)-2,5,8-trinitrazanonane (BNTNN), and FIGS. 7–12 illustrate the synthesis of 1,6-bis-(3',5'-dinitro-1',2',4'-triazolo)-2,5-dinitrahexane (BNDNH). Both of these nitramine compounds contain ethylene spacers between the nitraza moieties of the azaalkane chain. It has been found by the inventors that the incorporation of ethylene spacers in the chain unexpectedly produces superior sensitivity properties in the polynitramine. Although not illustrated, it is possible to produce higher homologues of these ethylene spaced polynitramines, as well as polynitramines with methylene spacers or spacers longer than ethylene spacers. The azaalkane chain may also be branched, with the branches optionally containing nitraza moieties and/or a terminal cite for nucleophilic substitution of a heterocyclic moiety. It is also within the scope of the invention to make a heterocyclomethyl nitrazaalkane having only a single heterocyclomethyl moiety. Another possibility is for one or more of the terminal moieties to be substituted with an energetic functionality other than a heterocyclomethyl group, for example, an azido group, so long as at least one heterocyclomethyl group is present in the nitramine molecule.

FIGS. 3–12 illustrate three processes for making polynitramines suitable for use in this invention.

The first process for preparing a polynitramine is illustrated in FIGS. 3, 5, 7, and 10, in which a polyamine is perchlorinated to convert the primary amine moiety or each of the primary amine moieties into a respective N-perchlorinated amine moiety having two chlorine atoms. Any secondary amine moiety is converted into an N-chlorinated amine moiety having one chlorine atom. The perchlorinated polyamine is then nitrated to substitute respective nitro moieties for one of the chlorine atoms of the N-perchlorinated amine moiety and for the chlorine atom of the N-chlorinated amine moiety. The polyamine is then dechlorinated to provide the polynitrazaalkane.

Suitable perchlorinating agents include, by way of example, sodium hypochlorite, N-chlorosuccinimide, calcium hydrochlorite, CHLORAMINE-T, or other N-chlorosulfonamides. The perchlorination may be performed in one or more solvents, especially water and/or a polar organic solvent. The perchlorination is preferably performed at room temperature or lower and may be followed by precipitation of the perchlorinated polyamine and filtering of the solvent. The nitration step may be performed with nitric acid, such as nitric acid having a concentration of 70 weight percent or higher, preferably 90 weight percent or higher. The nitration step may also be conducted at room temperature and may be followed by a precipitation and filtering. Dechlorination of the nitrated polyamine may be performed with an alkali metal hydroxide, such as sodium hydroxide, and is preferably followed by a pH adjustment to a range of 4 to 7 and additional filtering.

The second process for preparing a polynitramine is illustrated in FIGS. 4, 6, 8, and 11, in which a polyamine comprises at least one primary amine moiety and optionally at least one secondary amine moiety. According to this process, the polyamine is acylated under conditions to convert the primary amine moiety into a monoacylated amine moiety while leaving the secondary amine moiety nonacylated. The N-acylated polyamine is then nitrated to form one nitro group on each of the primary amine moieties and another nitro group on the secondary amine moiety. The primary moiety is then deacylated to provide the polynitrazaalkane.

The acylation step may be performed with acetic anhydride or other acyl anhydrides, as well as acid chlorides. The acyl group is represented by —C(O)R, wherein R may be, for example, hydrogen, an alkyl having 1 to 8 carbon atoms, or branched alkyls. Nitration may be formed with nitric acid, nitronium ion salts, mixed acids (sulfuric and nitric acids), acetic nitric anhydride, and a combination of trifluoroacetic anhydride and a nitrate source (e.g., ammonium nitrate). Deacylation may be accomplished by hydrolysis in water, or with caustic. These steps are described in George F. Wright, Part 1 of *Chemistry of the Nitro and Nitroso Groups*, pp. 614–680 (1969).

Figure 9:
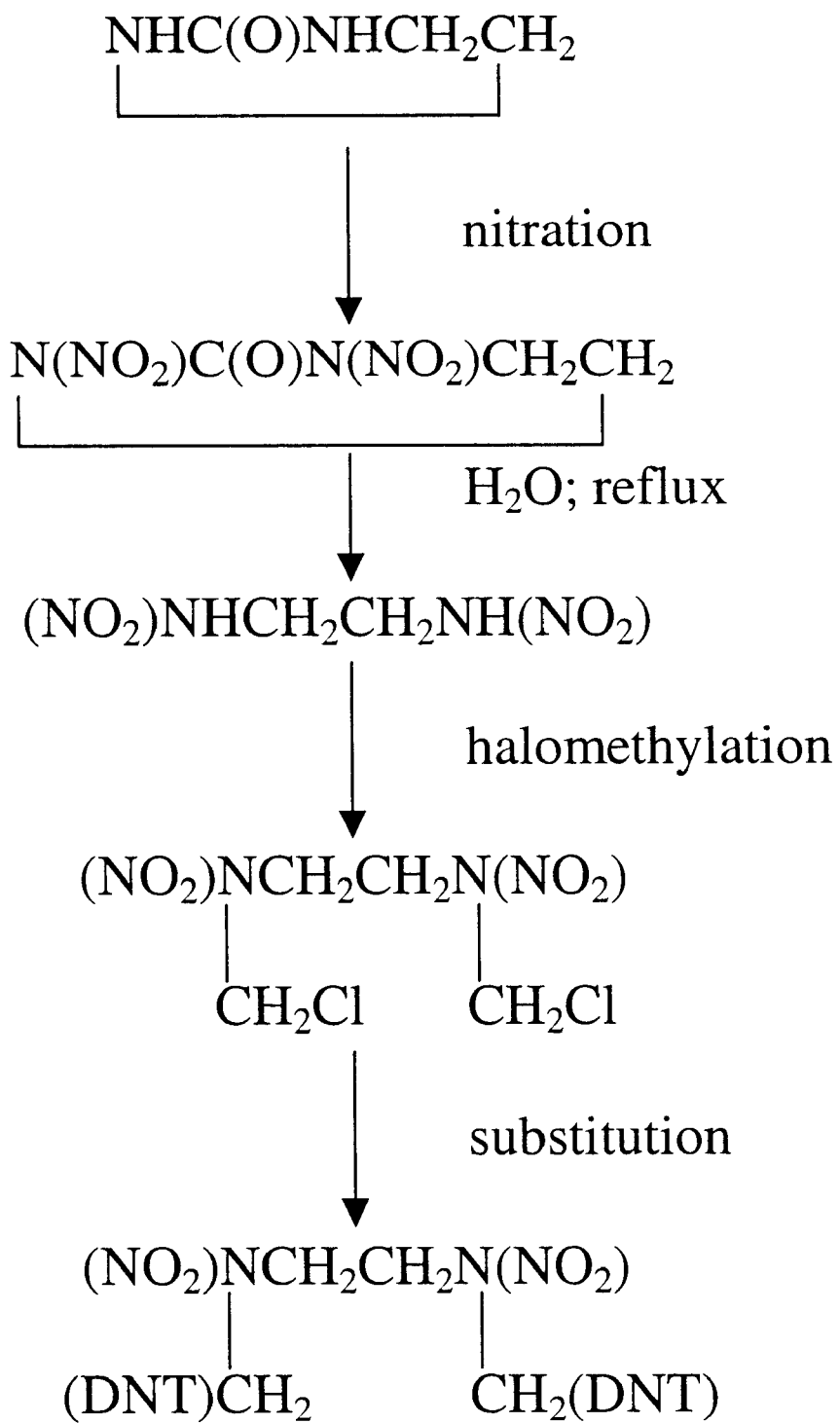
FIG. 9 is a flow chart setting forth a procedure for preparing 1,6-bis-(3',5'-dinitro-1',2',4'-triazolo)-2,5-dinitrahexane in accordance with another embodiment of the invention.
Figure 10:
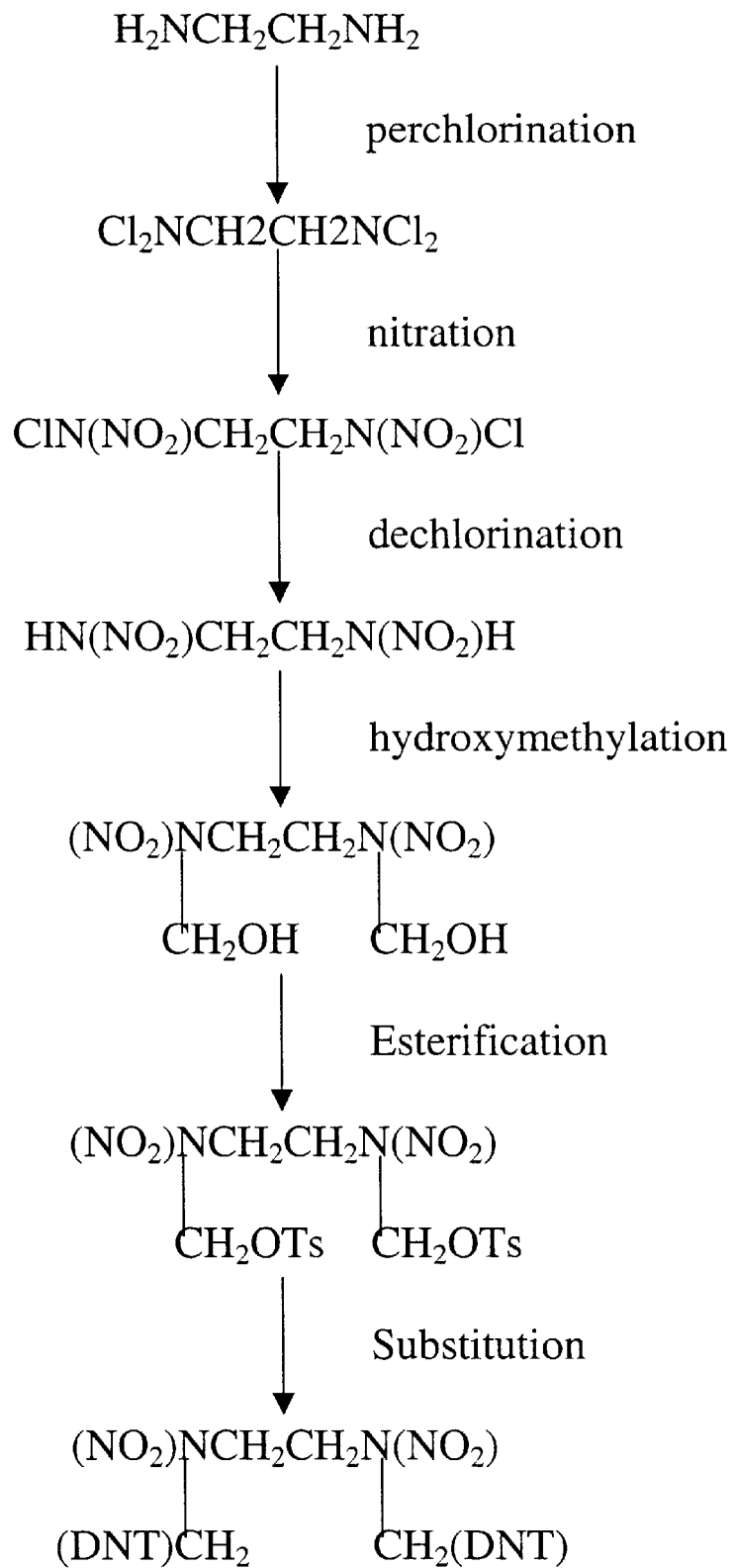
FIG. 10 is a flow chart similar to FIG. 5, setting forth a procedure for preparing 1,6-bis-(3',5'-dinitro-1',2',4'-triazolo)-2,5-dinitrahexane.
Figure 11:
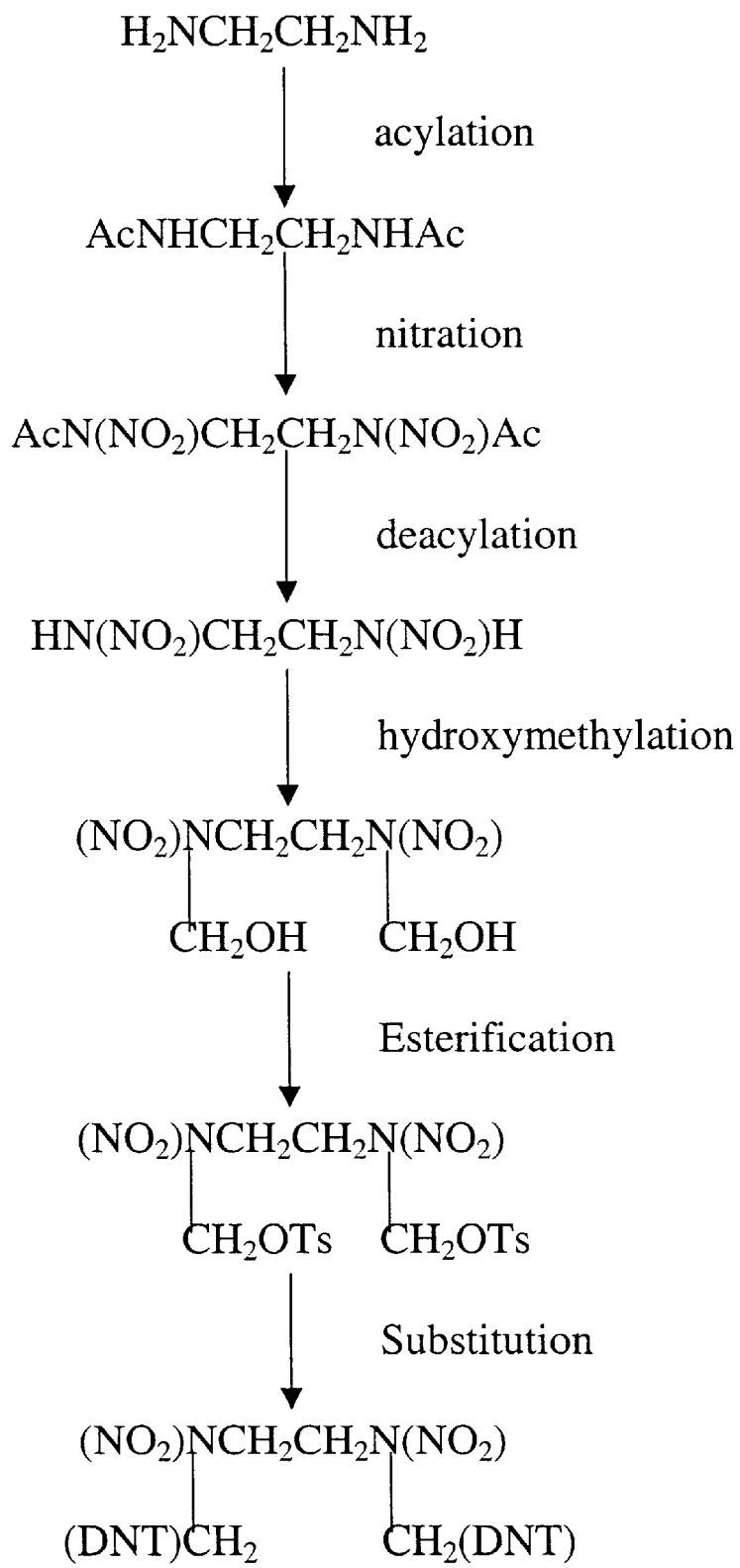
FIG. 11 is a flow chart similar to FIG. 6, setting forth a procedure for preparing 1,6-bis-(3',5'-dinitro-1',2',4'-triazolo)-2,5-dinitrahexane.
Figure 12:
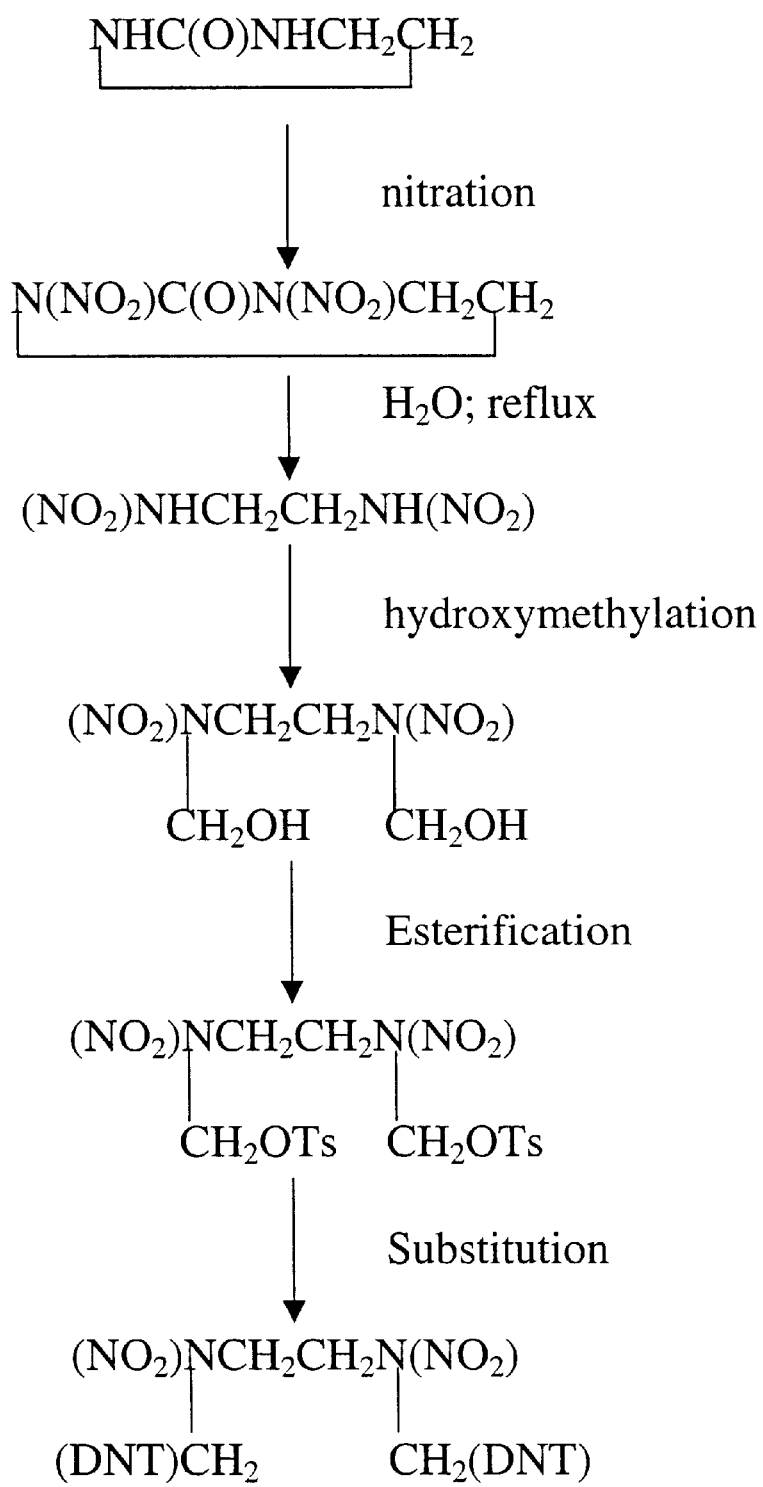
FIG. 12 is a flow chart setting forth a procedure for preparing 1,6-bis-(3',5'-dinitro-1',2',4'-triazolo)-2,5-dinitrahexane according to still another embodiment of the invention.

The third process for preparing a polynitramine is illustrated in FIGS. 9 and 12, in which imidazolidinone (or ethylene urea) is used to prepare 1,2-dinitrazaethylene. This may be carried out at room temperature or lower. The imidazolidinone is treated with the nitrating agent or mixture, which may be nitric acid, a mixed acid (sulfuric and nitric acids), and acetic nitric anhydride. Next, the reaction is quenched in a water bath over ice to precipitate the nitroacyl amine, which is then refluxed in water.

Exemplary nitramines made by this invention were found to possess the following properties:

| Formula | BNTH $C_8H_8N_{16}O_{14}$ | BNDP $C_7H_6N_{14}O_{12}$ | BNTNN $C_{10}H_{12}N_{16}O_{14}$ | BNDNH $C_8H_8N_{14}O_{12}$ |
|---|---|---|---|---|
| density (g/cc) (measured) | 1.80 | 1.845 | 1.773 | 1.8205 |

-continued

| Formula | BNTH $C_8H_8N_{16}O_{14}$ | BNDP $C_7H_6N_{14}O_{12}$ | BNTNN $C_{10}H_{12}N_{16}O_{14}$ | BNDNH $C_8H_8N_{14}O_{12}$ |
|---|---|---|---|---|
| $\Delta H_f$ kcal/mol (calculated) | +117 | +149.8 (measured) | +108.0 | +143.74 |
| ABL impact (cm) | 3.5 | 6.9 | 6.9 | 3.5 |
| ABL friction (lbs@fps) | 800@8 | 800@8 | 420@8 | 800@8 |
| TC ESD confined | 0.25 | >8 | 2.09 | 0.15 |
| TC ESD unconfined (J) | 8 No bulk ignition | 1 No bulk ignition | 8 mass ignition | 1 No bulk ignition |
| TC impact (in.) | 40 | 34.78 | 25.0 | 40.09 |
| TC friction (lbs) | >64 | >64 | >64 | >64 |
| SBAT | 225 | 280 | 225 | 225 |

Density was measured by a gas pycnometer.

The computational method for calculating heats of formation is described in George A. Olah and D. R. Squire, *Chemistry of Energetic Materials*, Chapt. 4, pp. 77–94 (Academic Press 1991), which is incorporated herein by reference for its teaching of this method.

The remaining properties were calculated or measured in accordance with R. B. Cragun, *Hazards Properties of a Magnesium Neutralized Propellant*", AIAA Paper No. AIAA-91-2860, which is incorporated herein by reference for its teaching of how to measure or calculate these properties.

Dinitrotriazole may be synthesized by nitrating 3,5-diamino-1,2,4-triazole in an acidic solution to form 3,5-dinitro-1,2,4-triazole. Nitrating may be performed with an alkali metal nitrite, such as sodium nitrite or potassium nitrite. The acid solution may comprise hydrochloric acid and/or sulfuric acid. 3,5-diamino-1,2,4-triazole may be obtained commercially or prepared in accordance with the teachings below. The dinitrotriazole is then extracted from the acidic solution. Suitable solvents for the extraction include methyl tert-butyl ether and a dialkyl ether (e.g., diethyl ether), and mixtures thereof. The acid solution is preferably maintained at a pH of not more than about 3 or less, preferably not more than about 2, and more preferably 1 to 2 during the nitration and extraction. If a salt is desired, the dinitrotriazole may be reacted with a suitable base at, for example, room temperature or lower. Representative bases include potassium carbonate, potassium bicarbonate, sodium bicarbonate, and sodium carbonate.

The family of DNT-disubstituted methylene nitramines have all been found to produce solvated crystals.

The following examples are offered to further illustrate the synthesis methods of the present invention. These examples are intended to be exemplary and should not be considered exhaustive of the scope of this invention.

EXAMPLES

Example 1

Preparation of 1,7-bis-(3',5'-dinitro-1',2',4'-triazolo)-2,4,6-trinitrazaheptane Step 1. Preparation of 1,7-diacetoxy-2,4,6-trinitrazaheptane In a 1 L, 3-neck round bottom flask equipped with a thermometer and condenser set at 15° C., 90 ml of 98% nitric acid and 240 ml of acetic anhydride were placed. Then, 67.2 grams of hexamine were dissolved in 110 ml of glacial acetic acid and added to the reaction flask via addition funnel, keeping the temperature at 15° C. to 20° C. The reaction was heated to 75° C. then allowed to cool to room temperature while stirring. After standing at room temperature for twelve hours, the solid was filtered and washed with acetic acid. Recrystallization from hot acetic acid yielded 88.42 grams of 1,7-diacetoxy-2,4,6-trinitrazaheptane.

Step 2. Preparation of 1,7-dichloro-2,4,6-trinitrazaheptane

In a 2 L 3-neck round bottom flask equipped with a thermometer and cooled to 5° C. were placed 783 grams of trifluoroacetic acid and 184 grams of concentrated HCl. To this solution, 88 grams of 1,7-diacetoxy-2,4,6-trinitrazaheptane were added. The reaction was stirred for overnight while allowing the reaction mixture to warm to room temperature. The product was filtered, washed with water and dried under vacuum to yield 64.42 grams of 1,7-dichloro-2,4,6-trinitrazaheptane.

Step 3. Preparation of 1,7-bis-(3',5'-dinitro-1',2',4'-triazolo)-2,4,6-trinitrazaheptane In a 1 L 3-neck flask equipped with a thermometer, condenser with drying tube, and argon purge were added 400 ml of acetonitrile and 7.0 grams of 1,7-dichloro-2,4,6-trinitrazaheptane. The mixture was stirred at room temperature until all solids dissolved. To this solution were added 9.7 grams of potassium dinitrotriazole and 4.7 grams of sodium bromide and the solution was stirred at room temperature until all solids dissolved. The reaction was heated to reflux overnight. The reaction was cooled to room temperature and solids removed by filtration. The solution was slowly dropped into water to precipitate a very flocculent solid, which was collected by filtration and dried under vacuum overnight at 45° C. to yield 12.2 grams of product in the form of a clathrate.

Example 2

Preparation of 1,9-bis-(3',5'-dinitro-1',2',4'-triazolo)-2,5,8-trinitrazanonane (BNTNN)

Step 1. Preparation of Diethylene Trinitramine

In a 5 L jacketed reactor cooled to 10° C. to 15° C. were placed 3 L of commercial chlorox with a titer of 4% NaOCl content. In a beaker 25.8 grams of diethylene triamine were dissolved in 100 ml of water followed by the careful addition of 45 ml of 12M HCl. The diethylene trinitramine solution thus prepared was then added to the reactor during the course of 5–10 minutes with vigorous stirring. The reaction was then extracted with chloroform 2 times with 50 ml solvent. The organic phases were combined and dried over sodium sulfate. To the chloroform solution, 51 ml of 98% nitric acid were added while keeping the temperature below 10° C. The reaction mixture was then stirred at 10° C. for ½ hour and subsequently warmed to 35° C. To the warmed nitrating mixture, 200 ml acetic anhydride were added drop-wise over 1 hour. Stirring was continued for ½ hour at 30° C. to 35 ° C. The chloroform was then evaporated in a stream of dry nitrogen gas during which the product crystallized. The solid was collected by filtration. The chloronitramine was next suspended in 1 L water and the pH adjusted to 12 with 50 ml 25% sodium hydroxide solution while monitoring with a pH meter. A thick oil remained that did not dissolve. Decantation away from the insoluble oil resulted in a cloudy caustic solution that was readjusted to pH 5.07 whereupon the product precipitated. The precipitant was collected, washed with water then dried under vacuum at ambient temperature. The yield was approximately 45% of theoretical.

Step 2. Preparation of 1,9-dichloro-2,5,8-trinitrazanonane

In a 5 L jacketed 3-neck reactor equipped with a top stirrer and thermocouple were placed 100 grams of diethylene trinitramine, 25.2 grams of paraformaldehyde and 1.5 L anhydrous dioxane. Dry HCl gas was added just under the reaction surface while keeping the temperature below 25° C. The reaction was initially very exothermic. HCl gas was added for 4 to 5 hours until the solution was almost clear. The solution was stirred overnight at 15° C., then HCl gas was added for 5 min until the solution was again clear. The solvent was evaporated in air and the pasty solid was dissolved by boiling in 1 L of chloroform. The chloroform solution was stirred over sodium sulfate to remove an insoluble yellow oil. The solvent was removed by rotary evaporation to yield 83 grams of pinkish-orange oil. The crude product was crystallized from chloroform.

Step 3. Preparation of 1,9-bis-(3',5'-dinitro-1',2',4'-triazolo)-2,5,8-trinitrazanonane In a 1 L round bottom flask at room temperature, 400 ml of acetonitrile were added, then 9.2 grams of 1,9-dichloro-2,5,8-trinitrazanonane were added. The slurry was stirred at ambient temperature until all of the solid had dissolved. To this solution were added 10.82 grams of potassium dinitrotriazole and 5.65 grams of sodium bromide. The reaction was stirred overnight at ambient temperature. The solvent was removed by rotary evaporation to yield 16.6 grams of a mixture that contained the crude product. The solid was suspended in water and extracted with ethyl acetate, washed with sodium bicarbonate and dried over magnesium sulfate. Evaporation of the solvent yielded 14.1 grams of clean product in the form of a clathrate.

Example 3

Preparation of 1,6-bis-(3',5'-dinitro-1',2',4'-triazolo)-2,5-dinitrazahexane (BNDNH)

Step 1. Preparation of Ethylene Dinitramine

In a 500 ml 3-neck round bottom flask equipped with a thermometer, magnetic stir bar and Argon inlet was placed 168 ml of 98% nitric acid, which was cooled to 0° C. To the acid was then added 83.6 grams of ethylene urea, portionwise, while keeping the temperature below 20° C. The reaction was then stirred under these conditions for 1 hour and subsequently allowed to warm to room temperature. The reaction was quenched in ice water and the precipitate that formed was collected by filtration. This product was added into approximately 1 L of boiling water in small portions. The temperature was maintained until no more gas was seen to evolve. The aqueous solution was cooled in an ice bath and the ethylene dinitramine product was collected by filtration. The reaction yield was 68% of theoretical of the dried product.

Step 2. Preparation 1,6-dichloro-2,5-dinitrazahexane

In a 5 L jacketed 3-neck reactor equipped with a top stirrer and thermocouple were placed 100 grams of ethylene dinitramine, 40 grams of paraformaldehyde and 1.5 L of dioxane. HCl gas was added to the reaction while keeping the temperature below 25° C. The reaction was initially very exothermic. The addition was continued for several hours until the product was consumed, as shown by NMR. The solvent was removed by rotary evaporation to yield a heavy oil. The crude 1,6-dichloro-2,5-dinitrazahexane product was dissolved in 300 ml of chloroform and cooled in an ice bath. The solid was collected by filtration and washed with chloroform. The product was air dried overnight. The reaction yield was 63.5%.

Step 3. Preparation of 1,6-bis-(3',5'-dinitro-1',2',4'-triazolo)-2,5-dinitrazahexane In a 500 ml round bottom flask at room temperature, 250 ml of acetonitrile and 3.4 grams of 1,6-dichloro-2,5-dinitrazahexane were added and stirred until all solid was dissolved. To this solution were added 5.5 grams of potassium dinitrotriazole and 3.1 grams of sodium bromide. The reaction was stirred for 2 days until the starting material was consumed, as shown by NMR. The solvent was removed by evaporation. The solid was dissolved in water, extracted with ethyl acetate, washed with brine, then dried over magnesium sulfate. The reaction yielded 3.2 grams of crude product in the form of a clathrate.

Example 4

Preparation of 1,5-bis(3,5-dinitro-1,2,4-triazolo)-2,4-nitrazapentane

Step 1. Preparation of Methylene bis(formamide)

50 grams (0.357 mol) of tetramine and an excess of formamide were heated to 140° C. for 5 hours. The reaction mixture was cooled, filtered, and washed with clean formamide. The solid was recrystallized from boiling ethanol to yield 16 grams (43%) of methylene bis(formamide) product. The liquor from the reaction mixture may be recycled in subsequent reactions (50.0 grams of tetramine, same reaction conditions) to afford greater yields of methylene bis (formamide).

Step 2. Preparation of Methylene bis(nitramine)

50.0 grams (0.490 mol) of methylene bis(formamide) was slurried in 186 ml of acetic anhydride while stirring at 5° C. 186 ml of nitric acid (96%) were added over a 1.5 hour period to the slurry, maintaining the reaction temperature between 5° C. to 10° C. during the addition. The reaction was stirred for 3 hours at the same temperature following complete addition of the nitric acid, and then was poured over an ice water bath (approximately 1 L). The precipitate was filtered off, washed with three 300 ml portions of cold (5° C.) water, and washed with three 300 ml portions of 2.0 N HCl. The solid was placed in a loosely covered beaker and allowed to stand overnight at room temperature. The carbonyl groups were slowly hydrolyzed off to give a solution of product in formic acid, hydrochloric acid, and water. The product was crystallized out of the solution at −30° C., filtered, and washed with a minimum amount of cold water. The product was dried under vacuum, with a yield of approximately 41 to 43 grams (62–65%).

Step 3. Preparation of 1,5-dichloro-2,4-nitrazapentane 88.3 grams of paraformaldehyde were suspended in 275 ml of glacial acetic acid and HCl (gas) was bubbled through for about 2 hours until the reaction solution was nearly homogeneous. A brief nitrogen purge removed excess HCl (gas) and 80.0 grams (0.588 mol) of methylene bis (nitramine) were added to the solution. HCl (gas) addition was resumed and continued for 1.5 hours. The methylene bis(nitramine) slowly dissolved during this time, with a slight increase in reaction temperature noted (reaction temperature rose from 25° C. to 36° C., and slowly decreased over time). The reaction was stirred for an additional 1.5 hours under nitrogen purge. The reaction was poured into 2.5 L of ice water to precipitate out the 1,5-dichloro-2,4-nitrazapentane product. The product was washed with several portions of cold water to remove most of the acetic acid. Typical yields were in the 50% range based on the methylene bis(nitramine). The product was very sensitive to acid and decomposed (turned to a viscous oil) over time in the presence of trace amounts of acid.

Step 4. Preparation of 1,5-bis(3,5-dinitro-1,2,4-triazolo)-2,4-nitrazapentane 25.4 grams (0.129 mol) of potassium 3,5-dinitro-1,2,4-triazole (KDNT) were slurried in 200 ml of acetonitrile/120 ml tetrahydrofuran (THF). The suspension was allowed to stir under nitrogen for 15 minutes, followed by addition of 10.0 grams (42.9 mmol) of 1,5-dichloro-2,4-nitrazapentane. The reaction was allowed to stir overnight (14 hours to 16 hours) and filtered, and the filtrate was subjected to removal of the solvents under reduced pressure. The resulting oil was taken up in 500 ml of ethyl acetate and washed consecutively with 100 ml saturated sodium bicarbonate solution and 100 ml of water. The ethyl acetate was dried over magnesium sulfate and filtered, and the solvent removed under reduced pressure.

Example 5

Purification of 1,5-bis(3,5-dinitro-1,2,4-triazolo)-2, 4-nitrazapentane

The 1,5-bis(3,5-dinitro-1,2,4-triazolo)-2,4-nitrazapentane was precipitated from tetrahydrofuran/dichloromethane and dried several hours under vacuum. A sample of about 5 grams was added to boiling methanol (500 ml) and stirred vigorously for about ½ hour until no more solid dissolved. The warm methanol was filtered to remove any undissolved solid (crude BNDP). The methanol was allowed to cool to room temperature, then cooled in an ice bath. Cold dichloromethane was added slowly to the cold methanol solution until a solid precipitated out. The solution was filtered, and the collected solid (BNDP) was washed with a small amount of cold methanol. The purified material was dried under vacuum for several hours.

Example 6

Purification of 1,7-bis-(3',5'-dinitro-1',2',4'-triazolo)-2,4,6-trinitrazaheptane (BNTH)

In 5 ml test tubes, 250 mg of BNTH were dissolved in 2 ml of various hot solvents. The homogeneous solutions were then added to various nonsolvents until the solution was turbid. The solvent mixtures were then cooled in an ice bath for 30 minutes, then examined for crystal growth. The combinations of solvents and non-solvents examined are shown below. The combination of THF and MTBE yielded crystals but traces of THF were never completely removed from samples. Methanol and methylene chloride was marginally successful, yielding very small crystals; however, large amounts of methanol were used due to the low solubility of BNTH in methanol.

| Solvents | Nonsolvents |
| --- | --- |
| Nitrobenzene | MTBE |
| Nitrobenzene | Ethanol |
| Nitrobenzene | Isopropanol |
| Nitrobenzene | Water |
| Nitromethane | MTBE |
| Nitromethane | Ethanol |
| Nitromethane | Isopropanol |
| Nitromethane | Water |
| Acetonitrile | Xylene |
| Acetonitrile | Water |
| Acetonitrile | Chlorobenzene |
| Acetonitrile | Toluene |
| *Methanol | Methylene chloride |
| THF | MTBE |

*60 ml methanol per gram used for solvation.

The effective yields were generally 20 to 50 weight percent, with the exception of methanol/methylene chloride, which was found to provide effective yields of up to 75 weight percent.

Example 7

Preparation of Potassium 3,5-dinitro-1,2,4-triazole (KDNT)

Step 1. 3,5-diamino-1,2,4-triazole (DAT)

20.0 grams (0.238 mol) of dicyandiamide were suspended in 50 ml water and stirred vigorously. Hydrazine sulfate (15.5 grams, 0.119 mol) was added, and the mixture was heated. When the temperature of the mixture reached 50° C., hydrazine hydrate (5.8 ml, 0.119 mol) was added, and the reaction was heated to 120° C. to 125° C. All of the solids slowly dissolved, and the reaction was allowed to stir at this temperature for 16 hours. After this time, a small amount of solid had formed in the reaction. Heating was discontinued and the reaction mixture was cooled to room temperature. The reaction was filtered and the precipitate was washed with 20 ml of cold (5° C.) water. The filtrate was concentrated on a rotary evaporator to near dryness. The resultant solid was washed with four 50 ml portions of 25% ethanol/tetrahydrofuran and dried under vacuum. The product yield of 55.4 grams indicates contamination with the side-product (ammonium sulfate). The isolated product was approximately 70–75% DAT.

Step 2. Potassium 3,5-dinitro-1,2,4-triazole (KDNT)

27.0 grams (~0.20 mol) of crude DAT (from the above procedure) was dissolved in 1.01 liters of 1.0 N HCl. A one-liter, three-neck round bottom flask was fitted with a nitrogen inlet adapter, overhead stirrer, and addition funnel. The flask was charged with 125.4 g (1.82 mol) of sodium nitrite and 150 ml of water and cooled to 4° C. The DAT/HCl solution was added dropwise over a 3.5 hour period (maintaining the reaction temperature at 4° C.). After complete addition of the DAT solution, the reaction was heated to 60° C. for 1.5 hours and cooled back down to 4° C. and 135 ml of 6.0 N HCl were added. The reaction was allowed to warm to room temperature and stir for 16 hours. The reaction was extracted with seven 100 ml portions of methyl tert-butyl ether (MTBE). The MTBE was stripped on a rotary evaporator until near dryness. The viscous, orange oil which remained (32.6 grams of crude 3,5-dinitro-1,2,4-triazole) was dissolved in 550 ml of acetone. 20.2 grams (0.20 mol) of potassium bicarbonate was added slowly to the acetone/DNT solution (vigorous bubbling ensued). This reaction mixture was filtered, and the acetone was removed under reduced pressure. The crude KDNT was dissolved in 150 ml of water. Some insoluble matter was filtered off, and the aqueous KDNT solution was concentrated to near dryness on a rotary evaporator. The solid residue was dissolved in minimum amount of water, to which cold isopropyl alcohol was added until a yellow-orange precipitate was observed. The KDNT was filtered and washed with cold isopropyl alcohol. Yield of KDNT was 20.3 grams (51%).

The foregoing detailed description of the preferred embodiments of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the spirit and scope of the appended claims.

What is claimed is:

1. A method for heterocyclomethylating a nitrazaalkane, the method comprising:

halogenating an N-acetoxymethyl nitrazaalkane having an azaalkane chain of at least five atoms to form an N-halomethyl nitrazaalkane, the N-halomethyl nitrazaalkane comprising at least one halomethyl moiety having a halogen atom, the halogen atom comprising a member selected from the group consisting of chlorine, bromine, and iodine;

substituting a heterocyclic nucleophile for the halogen atom of the N-halomethyl nitrazaalkane to form an N-heterocyclomethyl nitrazaalkane, said substituting taking place in a solvent that forms a clathrate with the N-heterocyclomethyl nitrazaalkane; and recovering the N-heterocyclomethyl nitrazaalkane from the clathrate by precipitation in a nonsolvent.

2. The method of claim 1, wherein the heterocyclic nucleophile comprises a triazole.

3. The method of claim 1, wherein the heterocyclic nucleophile comprises a triazole having at least one nitro substituent.

4. The method of claim 1, wherein the heterocyclic nucleophile comprises a triazole having two nitro substituents.

5. The method of claim 1, wherein the heterocyclic nucleophile comprises imidazole.

6. The method of claim 1, wherein the heterocyclic nucleophile comprises at least one member selected from the group consisting of mononitroimadizole, dinitroimidazole, and trinitroimidazole.

7. The method of claim 1, wherein the N-heterocyclomethyl nitrazaalkane comprises at least one pair of methylene-spaced nitramine moieties.

8. The method of claim 1, wherein the N-heterocyclomethyl nitrazaalkane comprises at least two pairs of methylene-spaced nitramine moieties.

9. The method of claim 1, wherein the N-heterocyclomethyl nitrazaalkane comprises two heterocyclomethyl groups.

10. The method of claim 1, wherein the N-heterocyclomethyl nitrazaalkane comprises an N-heterocylomethyl polynitrazaalkane, the N-heterocyclomethyl polynitrazaalkane comprising 1,5-bis-(3',5'-dinitro-1',2',4'-triazolo)-2,4-dinitrazapentane.

11. The method of claim 1, wherein the N-heterocyclomethyl nitrazaalkane comprises an N-heterocylomethyl polynitrazaalkane, the N-heterocyclomethyl polynitrazaalkane comprising 1,7-bis-(3',5'-dinitro-1',2',4'-triazolo)-2,4,6-trinitrazaheptane.

12. The method of claim 1, wherein the nonsolvent comprises a member selected from the group consisting of methanol and methylene chloride.

* * * * *

UNITED STATES PATENT AND TRADEMARK OFFICE
CERTIFICATE OF CORRECTION

PATENT NO.    : 6,603,018 B2
DATED         : August 5, 2003
INVENTOR(S)   : Thomas K. Highsmith et al.

It is certified that error appears in the above-identified patent and that said Letters Patent is hereby corrected as shown below:

<u>Title page,</u>
Item [56], References Cited, OTHER PUBLICATIONS, after "of" change "Methylenedinitramine" to -- Methylenebisamides --

<u>Column 2,</u>
Line 2, after "prior" and before "performing" insert -- to --

<u>Column 6,</u>
Line 31, change "cite" to -- site --

<u>Column 7,</u>
Line 51, change "cite" to -- site --

<u>Column 9,</u>
Line 33, change "*Propellant*"," to -- *Propellant,* --

<u>Column 13,</u>
Line 32, change "non-solvents" to -- nonsolvents --
Line 67, after "ml" and before "water" insert -- of --

Signed and Sealed this

Tenth Day of February, 2004

JON W. DUDAS
*Acting Director of the United States Patent and Trademark Office*